US012576097B2

(12) United States Patent
Wang et al.

(10) Patent No.: US 12,576,097 B2
(45) Date of Patent: Mar. 17, 2026

(54) **ANTI-TUMOR EFFECTIVE COMPONENT OF *HEDYOTIS DIFFUSA*, PREPARATION METHOD THEREFOR AND USE THEREOF**

(71) Applicant: Guangdong New Ear Life Technology Co., Ltd., Foshan (CN)

(72) Inventors: Yingfeng Wang, Foshan (CN); Ya Hong, Foshan (CN)

(73) Assignee: Guangdong New Ear Life Technology Co., Ltd., Guangdong (CN)

( * ) Notice: Subject to any disclaimer, the term of this patent is extended or adjusted under 35 U.S.C. 154(b) by 1093 days.

(21) Appl. No.: 17/624,781

(22) PCT Filed: Apr. 2, 2020

(86) PCT No.: PCT/CN2020/082880

§ 371 (c)(1),
(2) Date: Jan. 4, 2022

(87) PCT Pub. No.: WO2021/196105

PCT Pub. Date: Oct. 7, 2021

(65) Prior Publication Data

US 2022/0273687 A1 Sep. 1, 2022

(51) Int. Cl.

*A61K 31/7076* (2006.01)
*A61K 31/7048* (2006.01)
*A61K 36/748* (2006.01)

(52) U.S. Cl.

CPC ........ *A61K 31/7048* (2013.01); *A61K 36/748* (2013.01); *A61K 2236/333* (2013.01); *A61K 2236/39* (2013.01)

(58) Field of Classification Search

CPC ... A61K 36/748; A61K 36/7048; A61P 35/00; C07H 1/08; C07H 17/04
USPC ........................................................... 514/27
See application file for complete search history.

(56) References Cited

FOREIGN PATENT DOCUMENTS

| | | | | |
|---|---|---|---|---|
| CN | 101011481 A | | 8/2007 | |
| CN | 101096378 | * | 1/2008 | ......... A61K 31/7048 |
| CN | 101096378 A | | 4/2008 | |
| CN | 102218097 A | | 10/2011 | |
| CN | 108888674 A | | 11/2018 | |
| WO | 2008038849 A1 | | 4/2008 | |

OTHER PUBLICATIONS

Li et al., Authentication of the anti-tumor herb Baihuasheshecao with bioactive marker compounds and molecular sequences, Food Chemistry, 2010, pp. 1239-1245, 119, Elsevier Ltd.
Wang et al., Anti-tumor activity of Hedyotis diffusa Willd. in mice, Journal of Chinese Pharmaceutical Sciences, 2013, pp. 272-276, 22(3), China Academic Journal Electronic Publishing House.
Zhongfeng et al., Isolation and Purification Process of the Monomers in Hedyotis diffusa Effective Parts with Dynamic NM R Spectroscopy Methods, Journal of Capital Normal University, National Science Edition, Oct. 2014, pp. 37-42, 5, China Academic Journal Electronic Publishing House.
Zhang et al., The anti-tumor effect and bioactive phytochemicals of Hedyotis diffusa willd on ovarian cancer cells, Journal of Ethnopharmacology, 2016, pp. 132-139, 192, Elsevier Ireland Ltd.
Li, Studies on the Chemical Constituents of Hedyotis diffusa Willd. and its Anti-tumour Activity in Vitro, Database of Excellent Master's Dissertations in China Medical and Health Science and Technology, Mar. 15, 2017, No. 03, E057-178. 104 pages.
International Search Report; China National Intellectual Property Administration (ISA/CN); International Application No. PCT/CN2020/082880; Jan. 6, 2021; 7 pages.
Written Opinion of the International Searching Authority; China National Intellectual Property Administration (ISA/CN); International Application No. PCT/CN2020/082880; Jan. 6, 2021; 5 pages.
Chinese First Office Action; Chinese National Intellectual Property Administration; Chinese Application No. 202080000477.3; Feb. 23, 2021; 22 pages.
Chinese Second Office Action; Chinese National Intellectual Property Administration; Chinese Application No. 202080000477.3; Sep. 7, 2021; 4 pages.

* cited by examiner

*Primary Examiner* — Ganapathy Krishnan
(74) *Attorney, Agent, or Firm* — Taft Stettinius & Hollister LLP

(57) ABSTRACT

The present invention relates to the field of medicines, in particular to an anti-tumor effective component of *Hedyotis diffusa,* a preparation method therefor and the use thereof. Provided in the present invention is the use of one or a combination of kaempferol-3-O-[2-O-(6-O-E-feruloyl)-β-D-glucopyranose]-β-D-pyranose and E-6-O-p-coumaroylpaederoside methyl ester in tumor resistance or the preparation of an anti-tumor drug. The research of the present invention has shown that both a kaempferol-3-O-[2-O-(6-O-E-feruloyl)-β-D-glucopyranose]-β-D-pyranose compound monomer and an E-6-O-p-coumaroylpaederoside methyl ester compound monomer have very strong anti-tumor activity. In the in-vivo anti-tumor activity research, the inhibition rates thereof can reach 48.97% and 45.96%, respectively; and when both are combined to inhibit tumor cells, the research reveals that the two monomers have an obvious effect of synergistically inhibiting tumors.

3 Claims, 4 Drawing Sheets

ANTI-TUMOR EFFECTIVE COMPONENT OF *HEDYOTIS DIFFUSA*, PREPARATION METHOD THEREFOR AND USE THEREOF

CROSS-REFERENCE TO RELATED APPLICATIONS

This application is a U.S. National Phase of International PCT Application No. PCT/CN2020/082880, which was filed on Apr. 2, 2020, and which is incorporated by reference herein in its entirety.

TECHNICAL FIELD

The present disclosure relates to the field of medicines, in particular to an anti-tumor effective component of *Hedyotis diffusa* Willd and a preparation method therefor and use thereof.

BACKGROUND

*Hedyotis diffusa* Willd. is a plant in the genus *Hedyotis* (Rubiaceae), is widely distributed in subtropical regions, and grows in Yunnan, Guangxi, Guangdong, Fujian, Zhejiang, Jiangsu, Anhui and so on in China. The *Hedyotis diffusa* Willd has the main effects of clearing heat, detoxicating and diuresis. Pharmacological studies have shown that the *Hedyotis diffusa* Willd. has antibacterial, immunity-enhancing, anti-tumor and anti-aging effects. *Hedyotis diffusa* Willd. contains complex components, mainly anthraquinones, terpenoids, flavonoids, sterols, organic acids, polysaccharides, alkaloids, trace elements, amino acids and volatile components. The anthraquinones are mainly alizarin; the flavonoids are mainly quercetin and kaempferol, etc.; the terpenoids are mainly iridoids; the sterols are mainly β-sitosterol and stigmasterol; and the organic acids are ursolic acid, oleanolic acid and ferulic acid.

Malignant tumor is a serious threat to human life and health, and is the disease with the highest mortality rate in the world. With the change of people's life style and the aggravation of environmental pollution, the incidence of malignant tumors has been increasing year by year in recent years. *Hedyotis diffusa* Willd. has abundant anti-tumor active ingredients. At present, the main ingredients that have been reported to have anti-tumor activity are anthraquinones, terpenoids, flavonoids, sterols, organic acids, polysaccharides and volatile components. It will be have an important application value and broad development prospect to separate and extract the anti-tumor active substances from *Hedyotis diffusa* Willd. and develop the anti-tumor active substances into new drugs with anti-tumor efficacy. For this reason, based on the previous research, the effective parts of *Hedyotis diffusa* Willd. are extracted in the present disclosure, and after extensive research, the effective anti-tumor components of *Hedyotis diffusa* Willd. are separated, which is of great significance for the development of new anti-tumor drugs.

SUMMARY

Therefore, the technical problem to be solved by the present disclosure is to provide an anti-tumor effective component of *Hedyotis diffusa* Willd and a preparation method therefor and use thereof.

To this end, the present disclosure provides the following technical solutions:

In a first aspect, provided is a use of kaempferol-3-O-[2-O-(6-O-E-feruloyl)-β-D-glucopyranosyl]-β-D-galactopyranose and E-6-O-(p-coumaroyl) scandoside methyl ester, alone or in combination, in resisting tumor or in preparation of anti-tumor drugs.

Preferably, the tumors include liver cancer.

Preferably, a mass ratio of kaempferol-3-O-[2-O-(6-O-E-feruloyl)-β-D-glucopyranosyl]-β-D-galactopyranose to E-6-O-(p-coumaroyl)scandoside methyl ester in combination is 1:1-1:5 or 2:1-5:1.

Preferably, a mass ratio of kaempferol-3-O-[2-O-(6-O-E-feruloyl)-β-D-glucopyranosyl]-β-D-galactopyranose to E-6-O-(p-coumaroyl)scandoside methyl ester in combination is 1:2-1:5 or 2:1-5:1, preferably 1:2, 1:3, 1:4, 1:5, 2:1, 3:1, 4:1 or 5:1.

Preferably, a mass ratio of kaempferol-3-O[2-O-(6-O-E-feruloyl)-β-D-glucopyranosyl]-β-D-galactopyranose to E-6-O-(p-coumaroyl)scandoside methyl ester in combination is 3:1.

In a second aspect, provided is an anti-tumor effective component of *Hedyotis diffusa* Willd., comprising kaempferol-3-O-[2-O-(6-O-E-feruloyl)-β-D-glucopyranosyl]-β-D-galactopyranose and E-6-O-(p-coumaroyl)scandoside methyl ester.

Preferably, a mass ratio of kaempferol-3-O-[2-O-(6-O-E-feruloyl)-β-D-glucopyranosyl]-β-D-galactopyranose to E-6-O-(p-coumaroyl)scandoside methyl ester is 1:1-1:5 or 2:1-5:1.

Preferably, the mass ratio of kaempferol-3-O-[2-O-(6-O-E-feruloyl)-β-D-glucopyranosyl]-β-D-galactopyranose to E-6-O-(p-coumaroyl)scandoside methyl ester is 1:2-1:5 or 2:1-5:1, preferably, 1:2, 1:3, 1:4, 1:5, 2:1, 3:1, 4:1 or 5:1.

Preferably, the mass ratio of kaempferol-3-O-[2-O-(6-O-E-feruloyl)-β-D-glucopyranosyl]-β-D-galactopyranose to E-6-O-(p-coumaroyl)scandoside methyl ester is 3:1.

Preferably, the anti-tumor effective component of *Hedyotis diffusa* Willd. is prepared with a method comprising:

preparing coumaroyl scandoside methyl ester by:

dissolving an extract of *Hedyotis diffusa* Willd in a 3-7 vol % alcohol solution, loading the obtained solution to a macroporous resin to perform static adsorption, then eluting with a 8-12 vol % alcohol solution, a 18-22 vol % alcohol solution, a 28-32 vol % alcohol solution and a 38-42 vol % alcohol solution successively, collecting the eluate of the 38-42 vol % alcohol solution, and concentrating to obtain an effective part of *Hedyotis diffusa* Willd; and dissolving the obtained effective part of *Hedyotis diffusa* Willd. in a 15-25 vol % alcohol solution, separating by a gel chromatography column under reduced pressure, eluting with a 15-25 vol % alcohol solution, and collecting the obtained eluate to obtain an eluate containing E-6-O-(p-coumaroyl)scandoside methyl ester, and then eluting with a 45-55 vol % alcohol solution, and collecting the obtained eluate to obtain a solution containing kaempferol-3-O-[2-O-(6-O-E-feruloyl)-β-D-glucopyranosyl]-β-D-galactopyranose.

Preferably, the anti-tumor effective component of *Hedyotis diffusa* Willd. is prepared with a method comprising:

dissolving an extract of *Hedyotis diffusa* Willd. in a 5 vol % ethanol solution, loading the obtained solution to a macroporous resin to perform static adsorption, and then eluting with a 10 vol % ethanol solution, a 20 vol % ethanol solution, a 30 vol % ethanol solution and a 40 vol % ethanol solution successively, collecting the eluate of the 40 vol % ethanol solution, and concentrating to obtain an effective part of *Hedyotis diffusa* Willd.; and dissolving the obtained effective part of *Hedyotis diffusa* Willd. in a 20 vol % ethanol solution, separating by a gel chromatography column under reduced pressure, eluting with a 20 vol % ethanol solution, and collecting the obtained eluate to obtain an eluate containing E-6-O-(p-coumaroyl) scandoside methyl ester, and then eluting with a 50 vol % ethanol solution, and collecting the obtained eluate to obtain a solution containing kaempferol-3-O-[2-O-(6-O-E-feruloyl)-β-D-glucopyranosyl]-β-D-galactopyranose.

In a third aspect, provided is an anti-tumor pharmaceutical composition, comprising the anti-tumor effective component of *Hedyotis diffusa* Willd. described above.

Preferably, the anti-tumor pharmaceutical composition further comprises a pharmaceutically allowable drug excipient or carrier.

Preferably, the anti-tumor pharmaceutical composition is prepared into a preparation form selected from a liquid preparation and a solid preparation; preferably, the preparation form is selected from the group consisting of an injection solution, a drip solution, dissolved medicines, powder, oral liquid, sprays, powder injections, granules, tablets, sugar-coated tablets, film-coated tablets, enteric-coated tablets, orally disintegrating tablets, capsules, hard capsules, soft capsules, a buccal agent, granules, pills, dripping pills, pellets, paste, sublimed preparations or disintegrants.

The technical solutions of the present disclosure have the following advantages:

1. The present disclosure provides the use of kaempferol-3-O-[2-O-(6-O-E-feruloyl)-β-D-glucopyranosyl]-β-D-galactopyranose and E-6-O-(p-coumaroyl)scandoside methyl ester, alone or in combination, in resisting tumor or in preparation of anti-tumor drugs. The research of the present disclosure has shown that both a kaempferol-3-O-[2-O-(6-O-E-feruloyl)-β-D-glucopyranosyl]-β-D-galactopyranose monomer and an E-6-O-(p-coumaroyl)scandoside methyl ester compound monomer have strong anti-tumor activity. In the in-vivo anti-tumor activity research, E-6-O-(p-coumaroyl)scandoside methyl ester has an inhibition ratio of 48.97% at a dose of 5 mg/kg, and kaempferol-3-O-[2-O-(6-O-E-feruloyl)-β-D-glucopyranosyl]-β-D-galactopyranose also achieves an inhibition rate of 45.96%. When both are combined to inhibit tumor cells, the research reveals that the two monomers have an obvious effect of synergistically inhibiting tumors.

2. The present disclosure provides the anti-tumor effective component of *Hedyotis diffusa* Willd, comprising kaempferol-3-O-[2-O-(6-O-E-feruloyl)-β-D-glucopyranosyl]-β-D-galactopyranose and E-6-O-(p-coumaroyl)scandoside methyl ester. The anti-tumor effective component of *Hedyotis diffusa* Willd has an significant tumor inhibiting effect. It is found through the research that a significant anti-tumor effect is achieved when the mass ratio of kaempferol-3-O-[2-O-(6-O-E-feruloyl)-β-D-glucopyranosyl]-β-D-galactopyranose to E-6-O-(p-coumaroyl)scandoside methyl ester is 1:1-1:5 or 2:1-5:1, while the highest anti-tumor effect is achieved when the mass ratio of kaempferol-3-O-[2-O-(6-O-E-feruloyl)-β-D-glucopyranosyl]-β-D-galactopyranose to E-6-O-(p-coumaroyl)scandoside methyl ester of 3:1.

BRIEF DESCRIPTION OF THE DRAWINGS

In order to illustrate the technical solutions in the specific embodiments of the present disclosure or the prior art more clearly, the following is a brief description of accompanying drawings required to be used in the description of the specific embodiments or the prior art. It is obvious that the accompanying drawings in the following description are some of the embodiments of the present disclosure, and that other drawings can be obtained from these drawings without any creative work for a person of ordinary skill in the art.

DETAILED DESCRIPTION

Figure 1:
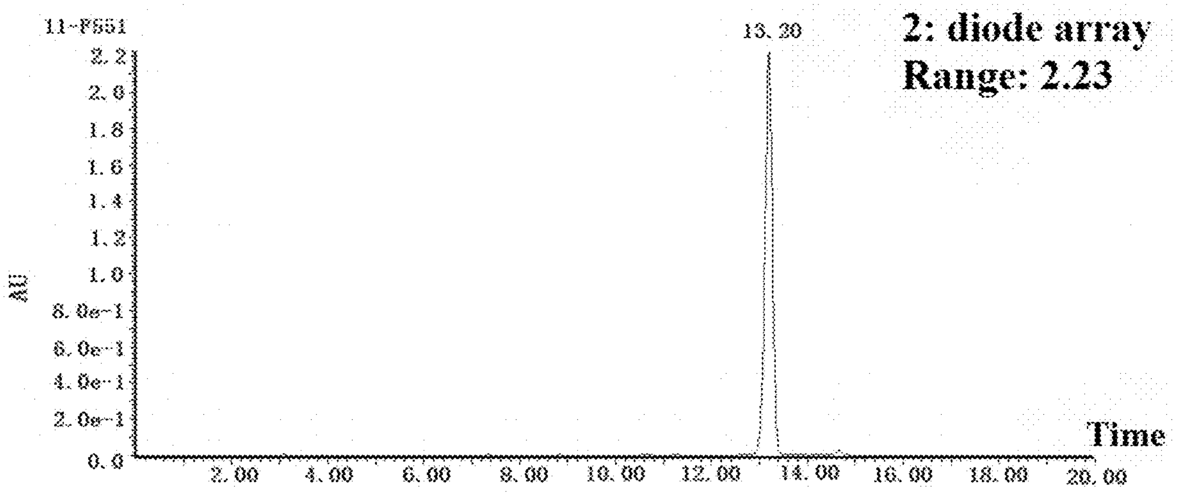
FIG. 1 is a liquid chromatogram of a monomer substance C in Embodiment 1 of the present disclosure.

The following embodiments are provided for a better understanding of the present disclosure, are not limited to the best embodiments, and do not constitute a limitation on the content and protection scope of the present disclosure. Any product that is identical or similar to the present disclosure obtained under an enlightenment of the disclosure or by combining the features of the disclosure with other prior art by anyone falls within the protection scope of the disclosure.

Experimental procedures or conditions that are not specifically indicated in the embodiments can be performed in accordance with the operations or conditions of conventional experimental procedures described in literatures in the art. The reagents or apparatus used, of which the manufacturer is not specified, are conventional reagent products available commercially.

Instruments: electronic balance (JT10001, GingJian), vacuum drying oven (ZK-82A, Shanghai Experimental Instruments General Factory), electrothermal blowing dry box (DL-101-ZBS, Tianjin Zhonghuan Experimental Electric Furnace Co., Ltd.), ultrasonic cleaner (KQ-250, Kunshan Ultrasonic Instrument Co. Ltd.), ultrasonic cleaner (KQ-500, Kunshan Ultrasonic Instrument Co. Ltd.), rotary evaporator (BüChi Rotavapor R-200, Sweden), water bath kettle (Changfeng, Beijing Changfeng Instrument Incorporation), extraction tank (HM1-50, Taiwan Hongquan Machinery Co., Ltd); LC-MS (Waters 2695: Dual λ Absorbance Detector, Sample manager, Binary solvent manager; MS: Micromass Q-Tof; MasslynessV4.0 workstation), NMR (Varian NMRs, 600 Hz), ultrasonic cleaner (KQ-250, Kunshan Ultrasonic Instrument Co., Ltd.), ultrapure water machine (pall), and electronic balance (Satorius);

Reagents: 95% ethanol, D-101 macroporous resin (Tianjin Nankai University Reagent Factory), n-butanol (Beijing Chemical Factory; batch number: 20090415), gel Sephadex-20, methanol, ultrapure water, organic filter membrane (0.45 um); methanol (Fisher, HPLC Grade, Fisher Scientific), acetonitrile (Fisher, HPLC Grade, Fisher Scientific), water (Wahaha ultrapure water). $CD_3OD$ (CIL).

Medicinal materials: *Hedyotis diffusa* Willd. medicinal materials (purchased from the medicinal material market in Anguo City, Hebei Province, China), identified by Prof. Chunsheng Liu of Beijing University of Chinese Medicine.

Embodiment 1 Preparation, Separation and Purification of an Anti-Tumor Effective Component of *Hedyotis diffusa* Willd

(1) Preparation of an Extract of *Hedyotis diffusa* Willd 2 kg of *Hedyotis diffusa* Willd medicinal materials were taken, added into 12 times volume (24 L) of 60 vol % ethanol solution, soaked overnight, and subjected to extraction under reflux at 80° C. for 2 hours, wherein the extraction was repeated to be performed for two times; and the extracts were mixed, concentrated by rotary evaporation, and dried to obtain the extract of *Hedyotis diffusa* Willd.

(2) Preparation of an Effective Part of *Hedyotis diffusa* Willd 10 g of the extract of *Hedyotis diffusa* Willd. prepared above was taken, dissolved in 50 ml of 5 vol % ethanol solution, and loaded to a D-101 macroporous resin to be statically adsorbed overnight after sample loading, then, elution was performed sequentially with a 10 vol % ethanol solution, a 20 vol % ethanol solution, a 30 vol % ethanol solution and 40 vol % ethanol solution in 3 to 5 times the column volume, the eluate of the 40 vol % ethanol solution was collected and concentrated by rotary evaporation, the concentrated solution was lyophilized into powder to obtain the effective part of *Hedyotis diffusa* Willd.

(3) Preparation of E-6-O-(p-coumaroyl)scandoside Methyl Ester and Kaempferol-3-O-[2-O-(6-O-E-feruloyl)-β-D-glucopyranosyl]-β-D-galactopyranose An LH-20 gel reduced-pressure chromatography column was equilibrated with a 20 vol % ethanol solution in 3 to 5 times the column volume at room temperature, and the effective part of *Hedyotis diffusa* Willd. was dissolved with a 20 vol % ethanol solution at a material to liquid ratio of 1:5 (g/ml), and loaded, wherein a sample loading volume is 2% of the column bed volume; elution was first performed with the 20 vol % ethanol solution, the eluate was collected to obtain a monomer C solution, and then elution was performed with a 50 vol % ethanol solution, and the eluate was collected to obtain a monomer F solution; and the resulting monomer C solution and the resulting monomer F solution were concentrated by rotary evaporation and lyophilized respectively to obtain a monomer C powder and a monomer F powder.

(4) Analysis and Identification

Liquid Chromatograph-Mass Spectrometer (LC-MS) and NMR were used to identify the monomer C powder and the monomer F powder obtained in the step (3) above, respectively. The monomer C powder and the monomer F powder were diluted with analytical grade methanol to prepare test solutions, respectively. The obtained test solutions were analyzed by liquid chromatography and mass spectrometry.

Chromatographic Conditions:

Chromatographic column: YMC-C18 column (250 mm×4.6 mm, 5 μm);

Mobile phase: a mobile phase A was water, a mobile phase B was acetonitrile, and the gradient elution conditions were listed in Table 1 below;

Flow rate: 1.0 mL/min;

Detection wavelength: 310 nm;

Column temperature: 35° C.; and

Injection volume: 10 μL.

TABLE 1

Liquid phase gradient elution conditions

| Time/min | A/% | B/% |
|---|---|---|
| 0 | 80 | 20 |
| 20 | 70 | 30 |

Mass Spectrometry Conditions:

Polarity: ESI-; Capillary: 2600 v; Source Temp: 80° C.; Desolvation Gas Flow: 600 L/h; Desolvation Gas Flow Temp: 300° C.; Collision Energy (MS): 10 v; Collision Energy (MSMS): 30 v; Flight Tube: 5630 v; MCP Detector: 2400 v.

Figure 2:
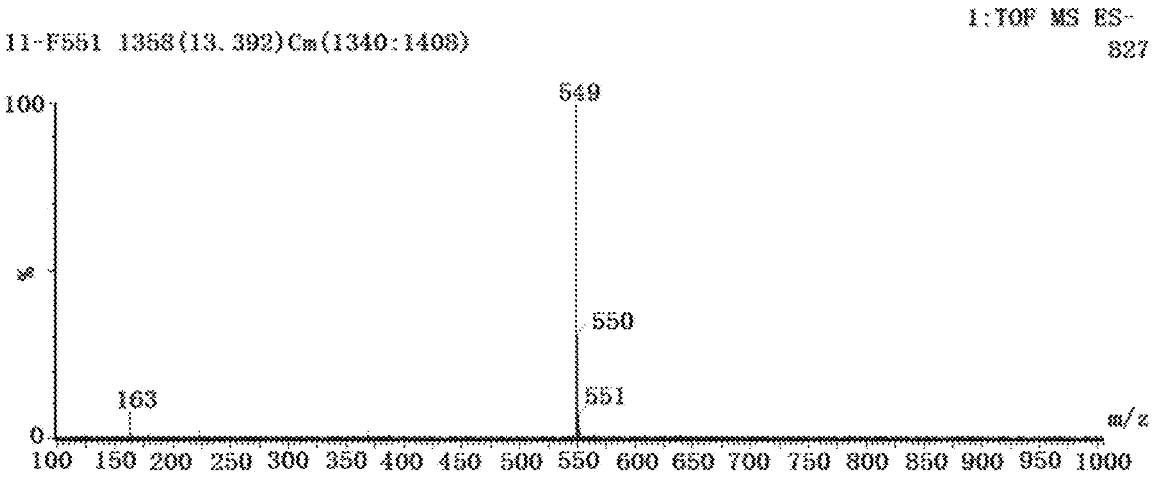
FIG. 2 is a mass spectrogram of the monomer substance C in Embodiment 1 of the present disclosure.
Figure 3:
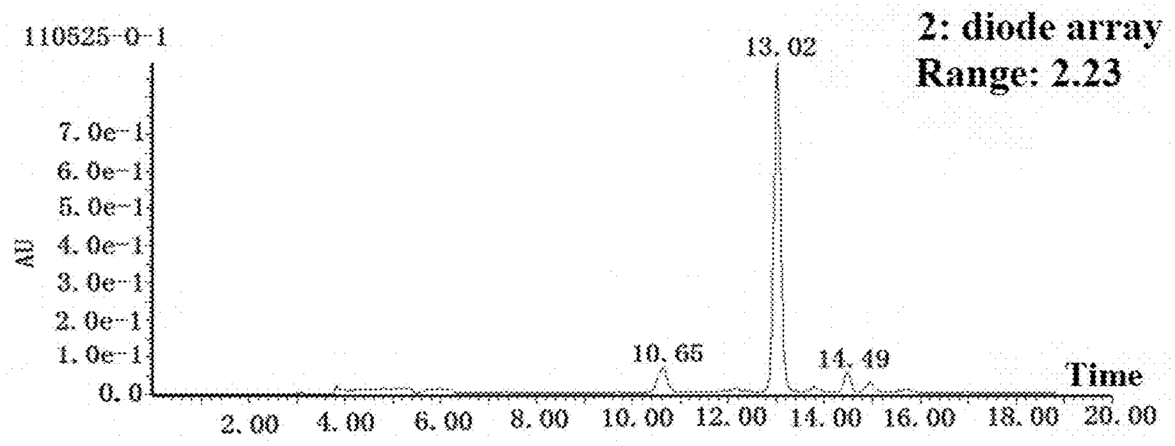
FIG. 3 is a liquid chromatogram of a monomer substance F in Embodiment 1 of the present disclosure.
Figure 4:
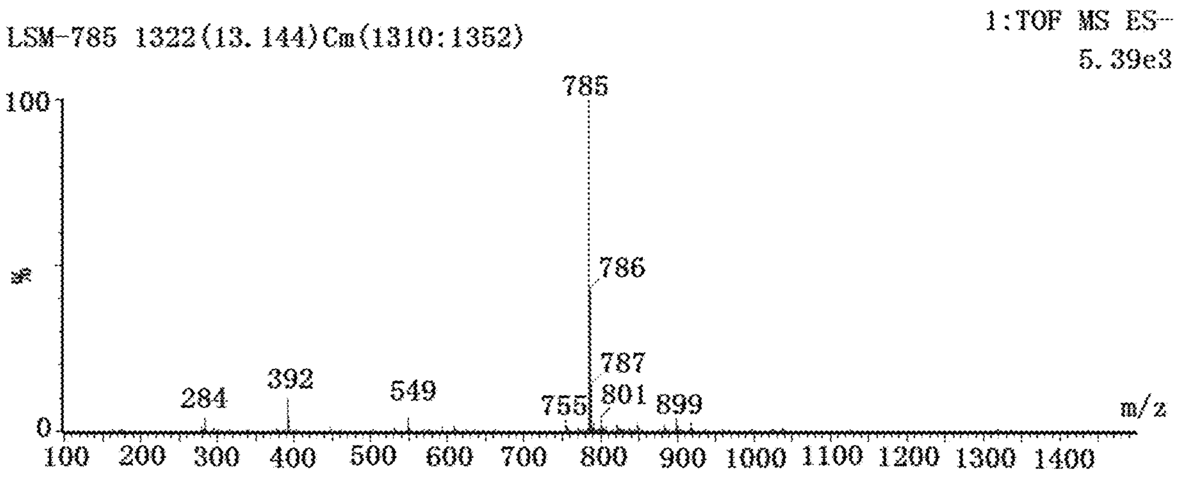
FIG. 4 is a mass spectrogram of the monomer substance F in Embodiment 1 of the present disclosure.

LC-MS Analysis Results:

A monomer substance C and a monomer substance F were subjected to LC-MS detection to obtain the corresponding liquid chromatogram and mass spectrogram. The molecular ion peaks and fragment peaks of the two substances were obtained and compared with those in the literature. The liquid chromatogram of the monomer substance C was shown in FIG. 1, and the mass spectrogram of the monomer substance C was shown in FIG. 2. The liquid chromatogram of the monomer substance F was shown in FIG. 3, and the mass spectrogram of the monomer substance F was shown in FIG. 4. The retention times and $[M-H]^-$ of the monomer substance C and the monomer substance F were shown in Table 2 below.

TABLE 2

Retention time and $[M-H]^-$ of each substance

| Peak No. | Retention time | $[M-H]^-$ |
|---|---|---|
| C | 13.20 | 549 |
| F | 13.02 | 785 |

NMR Results:

The carbon spectrum and hydrogen spectrum of the monomer substance C and the monomer substance F were analyzed, respectively, to obtain spectra for comparison. The hydrogen spectrum and HMQC data of the monomer substance C were shown in Table 3.

TABLE 3

| $^1H$ and HMQC data of the monomer substance C ($D_2O$, 600 MHz) | | | |
|---|---|---|---|
| $\delta_H$(ppm) | $\delta_C$(ppm) | $\delta_H$(ppm) | $\delta_C$(ppm) |
| 5.30 (1H, d, J = 6.0 Hz) | 97.9 | 3.00-3.40 | 71.5 |
| 7.50 (1H, brs) | 154.0 | 3.00-3.4 | 78.4 |
| | 110.0 | 3.87 (1H, dd, J = 12.0 Hz, 1.8 Hz) 3.64 (1H, dd, J = 12.0 Hz, 1.8 Hz) | 61.0 |
| 3.10-3.40 | 42.3 | 3.63 (3H, s) | 52.0 |
| 5.66 (1H, brs) | 83.6 | | 127.2 |
| 5.84 (1H, brs) | 127.7 | 7.45 (2H, d, J = 8.4 Hz) | 131.1 |
| | 150.4 | 6.80 (2H, d, J = 8.4 Hz) | 116.8 |
| 3.07 (1H, t, J = 7.2) | 46.9 | | 161.3 |
| 4.37 (1H, d, J = 15.0 Hz) | 62.7 | 6.80 (2H, d, J = 8.4 Hz) | 116.8 |
| 4.20 (1H, d, J = 15.0 Hz) | 169.1 | 7.45 (2H, d, J = 8.4 Hz) | 131.1 |
| 4.68 (1H, d, J = 7.8 Hz) | 97.9 | | 168.8 |
| 3.20-3.40 | 74.7 | 6.33 (1H, d, J = 16.2 Hz) | 115.4 |
| 3.20-3.40 | 77.9 | 7.61 (1H, d, J = 16.2 Hz) | 146.6 |

The hydrogen spectrum and HMQC data of the monomer substance F were shown in Table 4.

TABLE 4

| $^1H$ and HMQC data of the monomer substance F ($D_2O$, 600 MHz) | | | |
|---|---|---|---|
| $\delta_H$(ppm) | $\delta_C$(ppm) | $\delta_H$(ppm) | $\delta_C$(ppm) |
| | 151.2 | | 76.3 |
| | 131.5 | | 71 |
| | 177.2 | 4.65 (1H, d, J = 8.0 Hz) | 102.5 |
| | 160.1 | | |
| 6.08 (1H, brs) | 100.7 | | 75.7 |
| | 159.0 | | |
| | 102.5 | | 72.3 |
| | 120.9 | | 63.1 |
| 6.86 (2H, d, J = 8.8 Hz) | 115.7 | | 124.7 |
| | 160 | 7.11 (1H, brs) | 111.1 |
| 6.86 (2H, d, J = 8.8 Hz) | 115.5 | | 147.9 |
| 8.03 (2H, d, J = 8.8 Hz) | 130.5 | | 149.6 |
| 5.57(1H, d, J = 7.2) | 98.6 | 6.72 (1H, d, J = 8.0 Hz) | 115.7 |
| | 81.1 | 6.88 (1H, brd, J = 8.4 Hz) | 112.9 |
| | 73.3 | 7.45 (2H, d, J = 8.4 Hz) | 166.6 |
| 6.25 (1H, brs) | 94 | 6.20 (1H, d, J = 15.6 Hz) | 146.8 |
| 8.03 (2H, d, J = 8.8 Hz) | 130.9 | 3.76 (3H, s) | 57.0 |
| | 164.5 | 6.2 (1H, d, J = 15.6 Hz) | 112 |

Analysis of Results:

According to the comparison of the LC-MS data and NMR data with those in the known literature (Yongyong Zhang, Jiabo Luo. Study on chemical components of *Hedyotis diffusa* Willd. [J]. Chinese medicinal materials, 2008(4): 522), it can be concluded that the monomer substance C is E-6-O-(p-coumaroyl)scandoside methyl ester with the following structural formula:

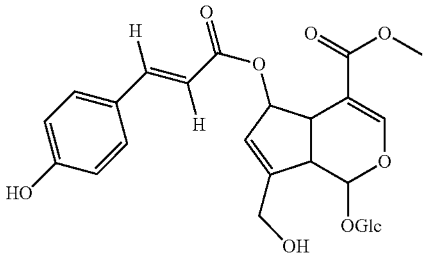

The monomer substance F is kaempferol-3-O-[2-O-(6-O-E-feruloyl)-β-D-glucopyranosyl]-β-D-galactopyranose with the following structural formula:

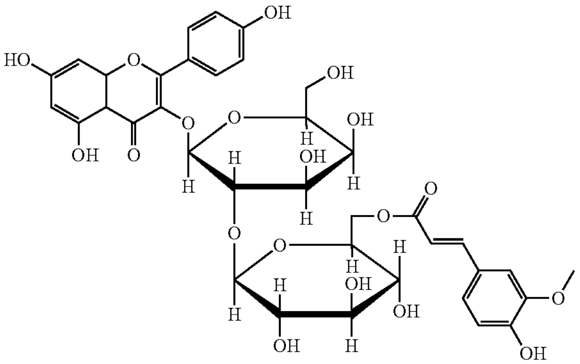

EXPERIMENTAL EXAMPLE 1

The purpose of this experimental example was to investigate the in-vivo anti-tumor effects of a single component C (E-6-O-(p-coumaroyl)scandoside methyl ester) and a single component F (kaempferol-3-O[2-O-(6-O-E-feruloyl)-β-D-glucopyranosyl]-β-D-galactopyranose).

1 Materials and Reagents 1.1 Experimental Animals

Male (female) ICR mice: Class II, provided by Beijing Vital River Laboratory Animal Technology Co., Ltd. (license No.: SCXK Jing 2007-0001).

1.2 Tumor Cell Lines Under Test

Solid tumor cell line S180 (presented by Beijing Dingguo Biotechnology Co., Ltd.).

1.3 Reagents and Equipment for Experiments 1.3.1 Reagents

Anhydrous ethanol: batch number, 20081026; purity, analytical purity; source, Beijing Huateng Chemical Co. Ltd.;

75% alcohol swab: self-prepared; and

Distilled water.

1.3.2 Equipment

Disposable sterile syringe: batch number, 071211; specification, 5 ml; source, Zhejiang Oujian Medical Equipment Co., Ltd.

Disposable sterile syringe: batch number, 080327; specification, 1 ml; source, Shanghai Kangshou Medical Equipment Co. Ltd.

Disposable sterile syringe: batch number, 080327; specification, 20 ml; source, Shanghai Kangshou Medical Equipment Co. Ltd.

Program-controlled autonomous activity box: made by the Institute of Pharmaceutical Research, Chinese Academy of Medical Science, 2IL-2;

Blood count analyzer: Shanghai Qiujing Biochemical Reagent Instrument Co., Ltd; measurements of Shanghai, 0202701113;

Microscope: XSD-A1; and

Gavage needle.

1.1 Drugs Under Test

The purified effective part (hereinafter referred to as the effective part) of *Hedyotis diffusa* Willd: prepared in the step (2) of Embodiment 1;

E-6-O-(p-coumaroyl)scandoside methyl ester (hereinafter referred to as methyl ester): prepared in the step (3) of Embodiment 1, purified and tested to have a purity of 98% or above;

Kaempferol-3-O-[2-O-(6-O-E-feruloyl)-β-D-glucopyranosyl]-β-D-galactopyranose (hereinafter referred to as kaempferol): prepared in the step (3) of Embodiment 1, purified and tested to have a purity of 98% or above;

p-coumaric acid (Aladdin Reagent Company).

1.2 Positive Control Drug

Cyclophosphamide: Chinese and Western Reagent Co. Ltd (100234-200502)

2 Methods 2.1 Cell Recovery and Passaging

Solid tumor cell line S180 cryopreservation tube were taken out from a liquid nitrogen tank and quickly placed into water at 37° C. with occasional shaking. After cryopreserved cell mother liquor was thawed, the lid edge of the cryopreservation tube was wiped with an alcohol swab. The thawed cell liquor was injected intraperitoneally into the peritoneal cavities of ICR mice by a syringe. The mice were kept at room temperature of 25±5° C., humidity of 60±10%, natural light, and free to ingest food and water. After about one week, ascites in the peritoneal cavities of the ICR mice were sucked by a syringe and injected into the peritoneal cavities of new ICR mice at a dose of 0.5 ml per mouse for passage for standby application.

2.2 Adaptive Feeding of ICR Mice

ICR class II mice, weighing about 18-22 g. Feeding conditions: room temperature of 25±5° C., humidity of 60±10%, natural light, free intake of water, and all mice were kept in the feeding environment for adaptive feeding for four days, fasted for 12 h before the experiment, free intake of water.

2.3 In-Vivo Seeding of Solid Tumor Cells S180

The experimental instruments were placed in a clean table and sterilized for about 30 min by turning on a UV lamp. The mice that were injected with ascites (about one week) were sacrificed by cervical dislocation, and abdomens of the mice were wiped with an alcohol swab. A 20 ml syringe was selected to suck the ascites (milky white is preferred) from the mice. The sucked ascites were placed in a sterile vial, and the vial was placed in a small box with ice. A certain amount of ascites was sucked onto a counting plate and placed under a microscope for counting, and the number of the cells was $10^7$ as a base for tumor inoculation (1:2) and passage (1:5).

The adaptively fed ICR class II male mice were taken, and wiped with an alcohol swab on the armpit areas of the right forelimbs. The axillary cavities of the right forelimbs of the mice were inoculated with diluted mice ascite cell ($10^7$ cells) suspension at 0.2 ml per mouse. After tumor inoculation, the mice were fed and watered freely. One hour later, the drug was administered by gavage.

2.4 In-Vivo Anti-Tumor Experiment After Tumor Inoculation in Mice

168 ICR class II male mice with a weight of 18-22 g were used. The mice were kept under the conditions of the item 2.2 for adaptive feeding for four days before the experiment. After four days, the mice were weighed and their autonomy was measured. The ICR mice were randomly divided into 14 groups, i.e.: a blank group, a model group, a positive drug control group, effective part 5, effective part 10, effective part 20, methyl ester 2.5, methyl ester 5, methyl ester 10, methyl ester 20, kaempferol 2.5, kaempferol 5, kaempferol 10, and kaempferol 20, 12 mice in each group. Each mouse was inoculated with S180 tumor according to the method in the item 2.3, and the drug was administered by gavage after inoculation.

A appropriate amount of test samples were weighed precisely, and prepared into test sample solutions having the desired concentrations by using a 5 vol % ethanol aqueous solution as a solvent, i.e.: the effective parts of 5 mg/kg, 10 mg/kg and 20 mg/kg correspond to the test sample solutions of the groups of the effective part 5, effective part 10, and effective part 20, respectively; E-6-O-(p-coumaroyl)scandoside methyl ester of 2.5 mg/kg, 5 mg/kg, 10 mg/kg, and 20 mg/kg correspond to the test sample solutions of the groups of methyl ester 2.5, methyl ester 5, methyl ester 10 and methyl ester 20, respectively; kaempferol-3-O-[2-O-(6-O-E-feruloyl)-β-D-glucopyranosyl]-β-D-galactopyranose of 2.5 mg/kg, 5 mg/kg, 10 mg/kg and 20 mg/kg correspond to the test sample solutions of the groups of kaempferol 2.5, kaempferol 5, kaempferol 10 and kaempferol 20, respectively. A appropriate amount of cyclophosphamide positive drug was weighed precisely, and prepared into a solution having a desired concentration by using a 5 vol % ethanol aqueous solution as a solvent, i.e., 20 mg/kg. The blank group was given a 5 vol % ethanol aqueous solution, the positive drug control group was given the cyclophosphamide solution, and the other groups were given the corresponding drugs and doses. Each mouse was administered by gavage at a dose of 0.2 ml/10 g. During the administration period, the mice were fed at 3 g/mouse and ingested water and food freely. All mice were continuously administered for 9 days, and sacrificed by decapitation on day 10. Blood, tumor, liver, spleen, and thymus of mice were collected. The blood collected was placed in a low temperature environment and sent out for blood check. The weight of the tumor, liver, spleen, and thymus and the size of the tumor were recorded.

2.5 In-Vivo Anti-Tumor Experiment of E-6-O-(p-coumaroyl)scandoside Methyl Ester and a Metabolite Thereof P-coumaric Acid 30 ICR class II male mice with a weight of 18-22 g were used. The mice were adaptively fed for four days under the conditions of the item 2.2 before the experiment. After four days, the mice were weighed and their autonomy was measured. The ICR mice were randomly divided into three groups, namely: a model group, methyl ester 10, p-coumaric acid 10, 10 mice in each group. Each mouse was inoculated with S180 tumor according to the method of the item 2.3, and the drug was administered by gavage after inoculation.

The appropriate amount of test samples were weighed precisely and prepared into test sample solutions having the desired concentrations by using a 5 vol % ethanol aqueous solution as a solvent, i.e.: E-6-O-(p-coumaroyl)scandoside methyl ester of 10 mg/kg; p-coumaric acid of 10 mg/kg. The appropriate amount of cyclophosphamide positive drug was weighed precisely and prepared into a solution having a desired concentration by using a 5 vol % ethanol aqueous solution as a solvent, i.e., 20 mg/kg. The blank group was given a solvent, the positive drug control group was given the cyclophosphamide solution, and the other groups were given the corresponding drugs and doses. Each mouse was administered by gavage at a dose of 0.2 ml/10 g. The mice were fed at 3 g/mouse and ingested water and food freely during the administration period. All mice were continuously administered for 9 days and sacrificed by decapitation on day 10. Blood, tumor, liver, spleen and thymus of the mice were collected. The blood obtained was placed in a low-temperature environment and sent out for blood check. The weight of the tumor, liver, spleen and thymus and the size of the tumor were recorded.

2.6 Data Processing

The recorded results were expressed as mean plus or minus standard deviation ($\overline{X}$±SD), and the data were analyzed by using statistical software SPSS 11.5 software.

3. Results

3.1 Results of In Vivo Anti-Tumor Experiments After Tumor Induction in Mice

Figure 5:
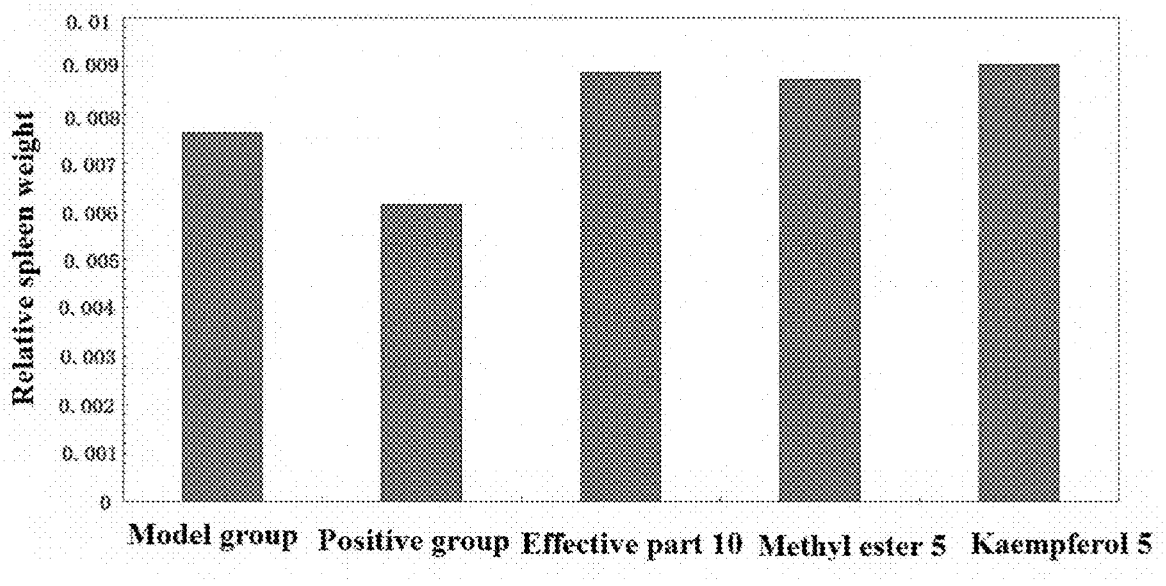
FIG. 5 is a graph of the relative spleen weight results of mice in an in-vivo anti-tumor experiment after tumor inoculation in Experimental Example 1 of the present disclosure.
Figure 6:
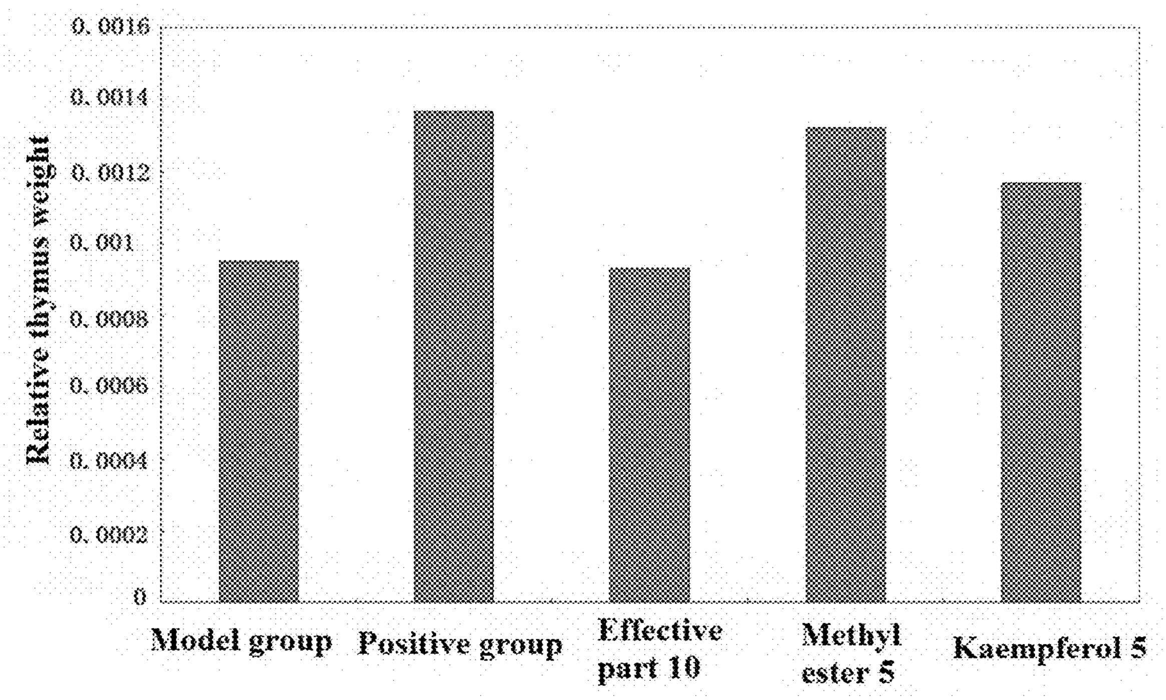
FIG. 6 is a graph of the relative thymus weight results of mice in the in-vivo anti-tumor experiment after tumor inoculation in Experimental Example 1 of the present disclosure.
Figure 7:
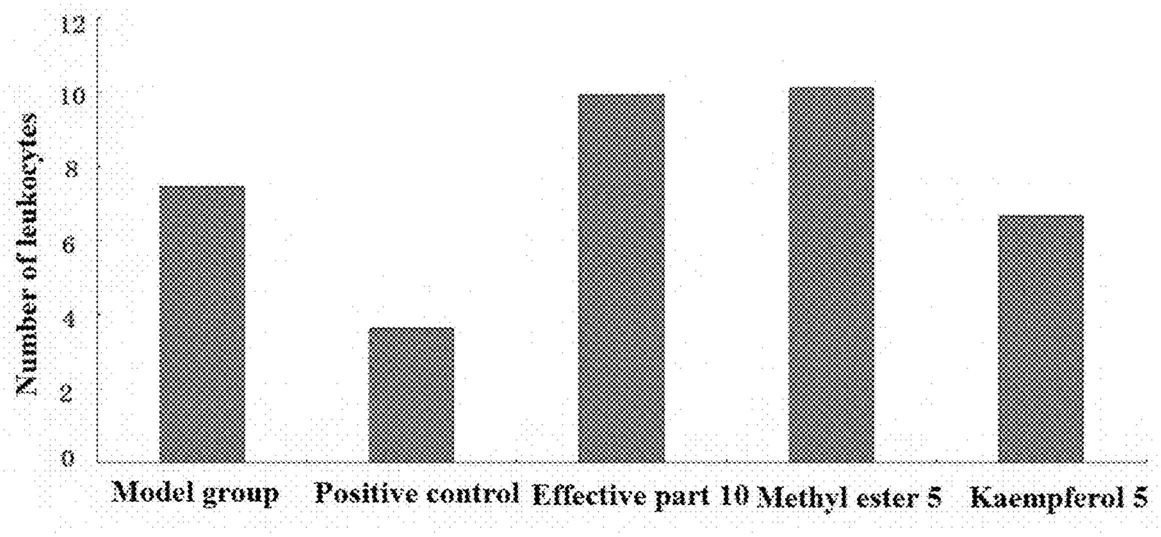
FIG. 7 is a graph showing a comparison result of the number of mouse leukocytes in the in-vivo anti-tumor experiment after tumor inoculation in Experimental Example 1 of the present disclosure.
Figure 8:
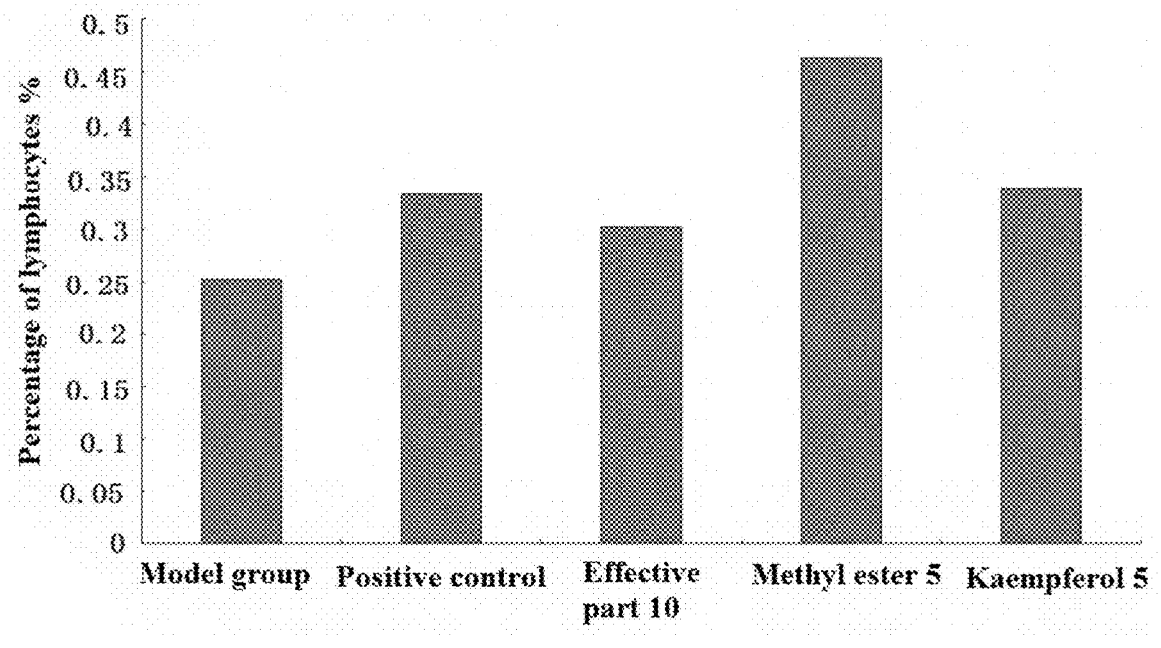
FIG. 8 is a graph showing a result of the percentage of mouse lymphocytes in the in-vivo anti-tumor experiment after tumor inoculation in Experimental Example 1 of the present disclosure.

As shown in Table 5, the positive control group, the effective part groups, the methyl ester groups and the kaempferol groups all showed significant anti-tumor activity, compared with the model group. Wherein, the inhibition rate in the positive control group (20 mg/kg) reached 57.19%. The inhibition rate of the methyl ester group and the kaempferol group also reached 40% or above at a dose of 5 mg/kg, and the inhibition rate of the methyl ester group at a dose of 5 mg/kg was the highest among the three test drugs, reaching 48.97%. The inhibition rate of the kaempferol group at a dose of 5 mg/kg also reached 45.96%. Meanwhile, it was found that there was a linear relationship between the dose and the inhibition rate in the experiment, and the inhibition rate of the three test drugs increased with the increase of the dose. However, after reaching a certain dose (and the best dose), the inhibition rate decreased with the increase of the dose. It can be seen that, the best dose of the effective part was 10 mg/kg, the best dose of the methyl ester was 5 mg/kg, and the best dose of the kaempferol was 5 mg/kg. In the experiment, the weight of spleen and thymus, the number of leukocytes in blood, and lymphocyte weight were compared in the three best dose groups, normal group, model group, and positive control group. The comparison results of spleen weights were shown in FIG. 5. Except for the positive control group, the relative spleen weight of mice in the effective part group at a dose of 10 mg/kg, in the methyl ester group at a dose of 5 mg/kg, and in the kaempferol group at a dose of 5 mg/kg showed an increase compared with that in the model group. Further, the relative spleen weight of mice in the kaempferol group at a dose of 5 mg/kg had the highest value, and the positive control group showed a decrease in relative spleen weight of mice. The comparison results of thymus weights were shown in FIG. 6. The relative thymus weight in the positive control group, in the methyl ester group at a dose of 5 mg/kg, and in the kaempferol group at a dose of 5 mg/kg showed an increase compared with that in the model group, and the relative thymus weight in the positive control group had the highest value, while the relative thymus weight in the effective part group at a dose of 10 mg/kg showed a decrease compared with that in the model group. The comparison results of the number of leukocytes were shown in FIG. 7. Compared with that in the model group, the number of leukocytes in the positive control group and in the kaempferol group at a dose of 5 mg/kg showed a significant decrease, while the number of leukocytes in the effective part group at a dose of 10 mg/kg and in the methyl ester group at a dose of 5 mg/kg showed a significant increase. The percentage of lymphocytes was shown in FIG. 8. Compared with the model group, the positive control group, effective part 10, methyl ester 5 and kaempferol 5 all showed an increase in the percentage of lymphocytes, while the percentage of lymphocytes in the methyl ester group at a dose of 5 mg/kg increased most significantly and was much higher than those in all of other groups.

TABLE 5

Inhibition rate of each group

| group | dose (mg/kg days) | relative tumor weight mean[a] ± SD $10^{-2}$ | inhibition rate (%) |
|---|---|---|---|
| Model group | — | 8.32 ± 2.56 | — |
| Positive control | 20 | 3.56 ± 0.77* | 57.19 |
| Effective part | 5 | 7.98 ± 2.07 | 4.02 |
| | 10 | 5.53 ± 3.42 | 33.52 |
| | 20 | 6.06 ± 2.08 | 27.31 |

TABLE 5-continued

| Inhibition rate of each group | | | |
|---|---|---|---|
| group | dose (mg/kg days) | relative tumor weight mean[a] ± SD $10^{-2}$ | inhibition rate (%) |
| Methyl ester | 2.5 | 6.49 ± 1.56* | 21.92 |
| | 5 | 4.24 ± 2.24* | 48.97 |
| | 10 | 5.81 ± 2.19* | 30.17 |
| | 20 | 5.98 ± 1.19* | 28.06 |
| Kaempferol | 2.5 | 7.01 ± 1.56 | 15.76 |
| | 5 | 4.49 ± 1.95 | 45.96 |
| | 10 | 6.04 ± 2.78 | 27.36 |
| | 20 | 5.59 ± 1.96 | 32.75 |

Positive control: cyclophosphamide

[a]Relative tumor weight mean = Σrelative tumor weight/number of tumor-bearing mice Relative tumor weight = actual tumor weight/body weight of tumor-bearing mice Statistical results are expressed as mean ± standard deviation ($\overline{X}$ ± S), n = 10. Significant differences between the drug administration groups and the model group are indicated as *P < 0.05.

3.2 In-Vivo Anti-Tumor Experiment of E-6-O-(p-coumaroyl)scandoside Methyl Ester and the Metabolite Thereof P-coumaric Acid As can be seen from Table 6, the inhibition rate of the p-coumaric acid group at a dose of 10 mg/kg was only 17.20% with no significant anti-tumor activity, while the inhibition rate of the methyl ester group at a dose of 10 mg/kg was 36.59% with significant anti-tumor activity, compared with that of the model group.

TABLE 6

| Comparison of anti-tumor activity of trans-(p-coumaroyl)scandoside methyl ester and p-coumaric acid | | | |
|---|---|---|---|
| Group | Dose (mg/kg) | Relative tumor weight mean[a] ± SD $10^{-2}$ | Inhibition rate (%) |
| Model group | — | 7.33 ± 1.24 | — |
| p-coumaric acid | 10 | 6.07 ± 2.91* | 17.20 |
| Methyl ester | 10 | 4.65 ± 3.29* | 36.59 |

[a]Relative tumor weight mean = Σrelative tumor weight/number of tumor-bearing mice Relative tumor weight = actual tumor weight/body weight of tumor-bearing mice Statistical results are expressed as mean ± standard deviation ( $\overline{X}$ ± S), n = 10.

Significant differences between the drug administration groups and the model group are indicated as *P < 0.05.

4. Summary and Discussion

In this experimental example, the in-vivo anti-tumor activities of E-6-O-(p-coumaroyl)scandoside methyl ester and kaempferol-3-O-[2-O-(6-O-E-feruloyl)-β-D-glucopyranosyl]-β-D-galactopyranose separated and purified from *Hedyotis diffusa* Willd. were investigated. The positive control drug was cyclophosphamide, and the inhibition rate of the positive control group reached about 60% at a dose of 20 mg/kg compared with the model group, indicating that the model was established successfully and the normal mice were well developed. Compared with the model group, the relationship between the dose of the effective part, methyl ester and kaempferol and the inhibition rate can be concluded under the condition that the experimental model was established. That is, within a certain dose range, the greater the dose, the greater the inhibition rate; while beyond the certain dose range, the inhibition rate had no significant change or was decreased slightly as the dose was increased. Here, the certain dose refers to the best dose for tumor inhibition. Through the above experiments, it was found that the best dose of the effective part was 10 mg/kg, the best dose of the methyl ester was 5 mg/kg, and the best dose of the kaempferol was 5 mg/kg. Meanwhile, it was found by comparing that the highest inhibition rate among these groups was present in the methyl ester group at a dose of 5 mg/kg, reaching 48.97%, and the inhibition rate also reached 45.96% in the kaempferol group, indicating that the two substances have strong anti-tumor activity.

Meanwhile, in this experimental example, the thymus and spleen of immune tissues of the body, as well as the number of leukocytes and the percentage of lymphocytes were compared in the groups. The results showed that the positive control group had the highest inhibition rate compared with the model group, but in the immune tissues, the relative spleen weight in the positive control group was lower than that in the model group. The number of leukocytes and erythrocytes in the positive control group was also lower than that in the model group. Based on the mechanism of the positive control drug, it was assumed that cyclophosphamide may phagocytize normal cells while phagocytizing tumor cells, resulting in a dramatic decrease in the number of erythrocytes and leukocytes, thereby presuming that the immune system of mice in the positive control drug group was somewhat disrupted. In the comparison, the methyl ester group at a dose of 5 mg/kg was the highest in terms of tissue weight, the number of leukocytes and the number of erythrocytes, and each index was much higher than that of the model group, which indicated that the methyl ester not only significantly improved the immune function of mice in a tumor inhibition process, but also achieved higher anti-cancer ability. The other two groups also showed an improvement compared with the model group.

Therefore, the methyl ester, as the most abundant substance in *Hedyotis diffusa* Willd., has been investigated for its in-vivo anti-tumor activity and immune system. This substance is fully demonstrated to have a strong anti-tumor activity and significantly improve the immune system of the body at a dose of 5 mg/kg. 5 mg/kg of kaempferol as a less abundant flavonoid also has a high anti-tumor activity, but fails to improve the immune system as much as that of the methyl ester.

In order to investigate the mechanism of an anti-cancer effect of the methyl ester, the inhibition rate of the methyl ester is compared with that of its metabolite p-coumaric acid. Results shows that the inhibition rate of p-coumaric acid is not significant, while the inhibition rate of the methyl ester is higher, thereby presuming that the absorption of the methyl ester is an important process during the action of the methyl ester, and the inhibition rate of p-coumaric acid is lower because p-coumaric acid is an acid and thus its absorption rate is not as high as that of esters such as methyl ester. Also, it is assumed that the components after hydrolysis of the methyl ester, except for p-coumaric acid, have a certain promotion effect on the absorption of anti-cancer drugs.

EXPERIMENTAL EXAMPLE 2

The purpose of this experimental example was to determine the inhibition rate of a flavonoid monomer (kaempferol-3-O-[2-O-(6-O-E-feruloyl)-β-D-glucopyranosyl]-β-D-galactopyranose) and an iridoid monomer (E-6-O-(p-coumaroyl)scandoside methyl ester) on human liver cancer Hep-G2 cells at different ratios.

1 Materials and Reagents 1.1 Experimental Drugs

E-6-O-(p-coumaroyl)scandoside methyl ester (hereinafter referred to as methyl ester): prepared in the step (3) of Embodiment 1, purified and tested to have a purity of 98% or above;

Kaempferol-3-O-[2-O-(6-O-E-feruloyl)-β-D-glucopyranosyl]β-D-galactopyranose (hereinafter referred to as kaempferol): prepared in the step (3) of Embodiment 1, and purified and tested to have a purity of 98% or above; and 5-fluorouracil.

1.2 Reagents

DMEM powder: Gibco; standard fetal bovine serum: Gibco, batch No. 1739464, 100 mL, stored at −20° C., and sealed; penicillin/streptomycin (double-antibody): Gibco, batch No. 1780186, 100 mL, stored at −20° C., and sealed; trypsin: Amresco, batch No. 1742078, 100 mL, stored at −20° C. and sealed; DMSO (mass spectrometry grade): Merck KGaA, batch No. 19947199813, 250 mL, stored in a cool place under shade and airtight conditions; PBS buffer solution: Gibco, batch No. 2098597, 500 mL, stored at 4° C., and sealed; 0.4% Trypan Blue staining solution: Invitrogen, batch No. 1189952, 1 mL, stored in a cool place under shade and airtight conditions; 5-fluorouracil, 100 g, stored in a cool place under shade and airtight conditions; CCK-8, 5 mL, stored at 4° C. under shade and airtight conditions.

1.3. Tumor Cell Lines Under Test

Human liver cancer Hep-G2 cells are commercially available.

1.4. Experimental Instrument

Microplate reader: Thermso Scientific Cellomics; $CO_2$ incubator: Thermo, Model 311; biological safety cabinet: NSF, Model 1389-A2; biological microscope: OLYMPUS 1, Model X71; fully automatic cell counter: Invitrogen; vertical pressure steam sterilizer: Model SN510C.

2. Experimental Method 2.1 Cell Recovery

A cryopreservation tube containing liver cancer Hep-G2 cells was taken out from a liquid nitrogen tank, quickly placed in a water bath at 38-39° C., and continuously shaken to be fully thawed within 1 min. The cryopreservation tube was centrifuged at 800 r/min for 9 min, and sprayed with 75% alcohol on the outside thereof, and then put into a ultra-clean table. The resulting supernatant was sucked and discarded. 1 ml of DMEM complete medium was added, and a mixture of the cells and the DMEM complete medium was blown evenly, and then the cells were transferred to a 25 ml culture dish. 6-8 ml of DMEM complete medium was added, and a mixture of the cells and the DMEM complete medium was gently blown evenly, and put into a constant temperature incubator at 37° C. with 5% $CO_2$.

2.2. Cell Passaging

The old medium in the item 2.1 was sucked out. 2 ml of PBS buffer solution was added, and the cells were washed by gently shaking the culture flask. The PBS buffer solution was sucked out to remove the loose, dead and senescent cells and their metabolic wastes, and the cells were washed for 2-3 times. 2 ml of trypsin was added, and the culture dish was gently shaken for 30 s. After the trypsin was sucked out, the culture dish was put into the incubator for full digestion for 3 min, and 2 ml of fresh DMEM complete culture was added. The cells were gently blown and dispersed into individual cells under a microscope, and then 6-8 ml of fresh DMEM complete medium was added and the cells were incubated in a constant temperature incubator.

2.3 Cell Plating 2 mL trypsin was added into the cells cultured in the item 2.2 in the logarithmic growth phase and the cells were digested for 30 s. After the trypsin was sucked out, the culture dish was placed into the incubator for full digestion for 3 min, and 2 mL of fresh medium was added. The cells were gently blown to disperse the cells into individual cells under the microscope. 10 μL of cell suspension and 10 μL of 0.4% Trypan blue staining solution were mixed well to fully stain the cells. 10 μL of the stained cell suspension was added to a cell counting plate, and the number of cells was counted by a fully automatic cell counter. The cell suspension was diluted to $2\times10^5$ cells/mL with a DMEM complete medium. 100 μL of cell suspension was sucked with a multichannel pipette and seeded into a 96-well plate and incubated in a constant temperature incubator at 37° C. with 5% $CO_2$ for 24 h.

2.4 Drug Configuration 30 mL of DMEM complete medium was accurately measured, 30 μL of DMSO was added, and uniform mixing was conducted to prepare 0.1% DMSO medium. 15 mg of methyl ester, 15 mg of kaempferol and 5 mg of 5-fluorouracil were accurately weighed in 10 mL disposable centrifuge tubes with caps, respectively, 5 mL of 0.1% DMSO medium was added in each centrifuge tube, and uniform mixing was conducted to prepare 3 mg/mL of methyl ester solution, 3 mg/mL of kaempferol solution, and mg/mL of 5-fluorouracil solution (positive control). The kaempferol solution and the methyl ester solution having the above concentrations were uniformly mixed to prepare drug solutions having the desired ratio based on the mass ratio of kaempferol to methyl ester being 1:1, 1:2, 1:3, 1:4, 1:5, 5:1, 4:1, 3:1 and 2:1, 400 μL of each drug solution. 1 mg/mL of 5-fluorouracil solution was diluted to a concentration of 800, 600, 400, 200, 100, 50, 25 μg/mL, respectively, 400 μL of each drug solution.

2.5. Cell Dosing

The old medium in the 96-well plate in the item 2.3 was sucked out, and 100 μL of PBS buffer solution was added to each well to remove the loose, dead and senescent cells and their metabolic wastes. After that, the PBS buffer solution was sucked out. 100 μL of the prepared drug solution was added to each well, 3 wells in parallel. A negative control was set up, in which an equal volume of DMEM complete medium containing 0.1 vol % DMSO was added to each well, 3 wells in parallel. A blank control was a DMEM complete medium containing 0.1 vol % DMSO free of cells, 3 wells in parallel. The cells were incubated for 24 h in a constant temperature incubator at 37° C. with 5% $CO_2$.

2.6 Determination of Inhibition Rate

The DMEM complete medium containing 0.1 vol % DMSO in the drug solutions and negative control in the 96-well plate in the item 2.5 were sucked out. 100 μL, of PBS buffer solution was added to each well to remove the loose, dead and senescent cells and their metabolic wastes, and the original drug solutions was washed to be clean. The PBS buffer solution was sucked out, and the cells were washed twice; 100 μL of DMEM medium and 10 μL of CCK-8 dye solution were added to each well, well shaking was conducted, and the cells were incubated for 3 h in a constant temperature incubator at 37° C. with 5% $CO_2$. After incubation, the absorbance of each well in the 96-well plate was measured at a wavelength of 254 nm in a microplate reader, and steps 2.3 to 2.6 were repeated for three times.

2.7 Calculation of Inhibition Rate

The OD values of each drug administration group, the blank control group and the negative control group were expressed as a mean value±standard deviation (X±S), and the following formula was used to calculate the inhibition rate of the drugs on human liver cancer Hep-G2 cells.

Inhibition rate=(OD value of blank control−OD value of drug administration group)/(OD value of blank control−OD value of negative control)×100%.

3 Experimental Results 3.1 Positive Control Results

TABLE 7

| Group | Drug concentration (μg/mL) | Number of wells (n) | OD value | Inhibition rate % |
|---|---|---|---|---|
| Blank control | — | 6 | 0.178 ± 0.029 | — |
| Negative control | — | 6 | 1.623 ± 0.120 | — |
| | 25 | 3 | 1.517 ± 0.099 | 7.34 |
| | 50 | 3 | 1.459 ± 0.090 | 11.34 |
| | 100 | 3 | 1.422 ± 0.083 | 13.91 |
| 5-Fluorouracil | 200 | 3 | 1.366 ± 0.119 | 17.78 |
| | 400 | 3 | 1.052 ± 0.123 | 39.52 |
| | 600 | 3 | 0.812 ± 0.090 | 56.12 |
| | 800 | 3 | 0.734 ± 0.066 | 61.52 |
| | 1000 | 3 | 0.641 ± 0.069 | 67.96 |

Positive control results 3.2 The Results of the 1st Measurement

TABLE 8

Results of the 1st measurement

| Group | Drug ratio | Number of wells (n) | OD value | Inhibition rate % |
|---|---|---|---|---|
| Blank control | — | 3 | 0.183 ± 0.001 | — |
| Negative control | — | 3 | 2.668 ± 0.023 | — |
| Flavonoid monomer | — | 3 | 2.203 ± 0.027 | 18.69531 |
| Iridoid monomer | — | 3 | 2.480 ± 0.051 | 7.557677 |
| | 1:1 | 3 | 2.188 ± 0.025 | 19.3159 |
| | 1:2 | 3 | 1.928 ± 0.055 | 29.77867 |
| | 1:3 | 3 | 1.718 ± 0.017 | 38.22938 |

TABLE 8-continued

Results of the 1st measurement

| Group | Drug ratio | Number of wells (n) | OD value | Inhibition rate % |
|---|---|---|---|---|
| Flavonoid monomer:iridoid monomer | 1:4 | 3 | 1.998 ± 0.036 | 26.96177 |
| | 1:5 | 3 | 2.078 ± 0.017 | 23.74245 |
| | 2:1 | 3 | 2.088 ± 0.070 | 23.34004 |
| | 3:1 | 3 | 1.968 ± 0.017 | 28.16901 |
| | 4:1 | 3 | 2.308 ± 0.027 | 14.48692 |
| | 5:1 | 3 | 2.588 ± 0.046 | 3.219316 |

3.3 The Results of the 2nd Measurement

TABLE 9

Results of the 2nd measurement

| Group | Drug ratio | Number of wells (n) | OD value | Inhibition rate % |
|---|---|---|---|---|
| Blank control | — | 3 | 0.176 ± 0.037 | — |
| Negative control | — | 3 | 1.634 ± 0.027 | — |
| Flavonoid monomer | — | 3 | 1.458 ± 0.011 | 12.06612 |
| Iridoid monomer | — | 3 | 1.553 ± 0.025 | 5.564738 |
| | 1:2 | 3 | 1.092 ± 0.008 | 37.15084 |
| | 1:3 | 3 | 1.072 ± 0.025 | 38.54749 |
| | 1:4 | 3 | 1.011 ± 0.013 | 42.73743 |
| | 1:5 | 3 | 1.035 ± 0.032 | 41.06145 |
| | 2:1 | 3 | 1.109 ± 0.023 | 36.03352 |
| | 3:1 | 3 | 1.052 ± 0.016 | 39.94413 |
| | 4:1 | 3 | 1.067 ± 0.008 | 38.82682 |
| | 5:1 | 3 | 1.069 ± 0.013 | 38.73743 |

3.4 Results of the 3rd Measurement

TABLE 10

Results of the 3rd measurement

| Group | Drug ratio | Number of wells (n) | OD value | Inhibition rate % |
|---|---|---|---|---|
| Blank control | — | 3 | 0.180 ± 0.028 | — |
| Negative control | — | 3 | 2.367 ± 0.034 | — |
| Flavonoid monomer | — | 3 | 1.945 ± 0.037 | 19.28375 |
| Iridoid monomer | — | 3 | 2.208 ± 0.021 | 7.272727 |
| | 1:1 | 3 | 2.134 ± 0.024 | 10.66667 |
| | 1:2 | 3 | 1.609 ± 0.020 | 34.66667 |
| | 1:3 | 3 | 1.4639 ± 0.013 | 41.33333 |
| Flavonoid monomer:iridoid monomer | 1:4 | 3 | 1.929 ± 0.048 | 20.12570 |
| | 1:5 | 3 | 2.009 ± 0.033 | 16.36328 |
| | 2:1 | 3 | 1.589 ± 0.017 | 35.55307 |
| | 3:1 | 3 | 1.497 ± 0.026 | 39.78212 |
| | 4:1 | 3 | 1.576 ± 0.022 | 36.15642 |
| | 5:1 | 3 | 1.629 ± 0.037 | 33.75978 |

4. Discussion of the Results

It was found that kaempferol-3-O-[2-O-(6-O-E-feruloyl)-β-D-glucopyranosyl]-β-D-galactopyranose and E-6-O-(p-coumaroyl)scandoside methyl ester had inhibitory effects on human liver cancer Hep-G2 cells by three assays, and the inhibitory effects were different in different ratios. In the first experiment, the highest inhibition rate was 38.23% when the ratio of kaempferol-3-O-[2-O-(6-O-E-feruloyl)-β-D-glucopyranosyl]-β-D-galactopyranose to E-6-O-(p-coumaroyl) scandoside methyl ester was 1:3 and the relatively high inhibition rates were 29.78% and 28.17%, respectively when the ratios were 1:2 and 3:1; in the second experiment, the highest inhibition rate was 42.73% when the ratio of kaempferol-3-O-[2-O-(6-O-E-feruloyl)-β-D-glucopyranosyl]-β-D-galactopyranose to E-6-O-(p-coumaroyl)scandoside methyl ester was 1:4, and the relatively high inhibition rates were 41.06% and 39.94%, respectively when the ratios were 1:5 and 3:1; in the third experiment, the highest inhibition rate was 41.33% when the ratio of kaempferol-3-O-[2-O-(6-O-E-feruloyl)-β-D-glucopyranosyl]-β-D-galactopyranose to E-6-O-(p-coumaroyl)scandoside methyl ester was 1:3, and the relatively high inhibition rate was 39.78% when the ratio was 3:1. In the three experiments, the best inhibition ratio was a ratio of kaempferol:methyl ester=1:3 in both the first and third experiments, but the results of the second experiment were different, as the best inhibition ratio was present at a ratio of kaempferol:methyl ester=1:4. However, the inhibition rate at a ratio of kaempferol:methyl ester=3:1 was relatively high in all three experiments and the results were stable. In the three experiments, the inhibition rate at the ratio of kaempferol:methyl ester=3:1 was higher than those of kaempferol-3-O-[2-O-(6-O-E-feruloyl)-β-D-glucopyranosyl]-β-D-galactopyranose and E-6-O-(p-coumaroyl)scandoside methyl ester in all experiments.

Obviously, the above embodiments are merely examples for the purpose of clarity and are not meant to limit the implementation. Other variations or changes in different forms may be made based on the above description for those of ordinary skill in the art. It is not necessary, nor is it possible, to give an exhaustive list of embodiments. The obvious variations or changes derived therefrom still fall within the protection scope of the disclosure.

What is claimed is:

1. A method for resisting tumor, comprising administering kaempferol-3-O-[2-O-(6-O-E-feruloyl)-β-D-glucopyranosyl]-D-galactopyranose and E-6-O-(p-coumaroyl)scandoside methyl ester in combination to a subject in need, wherein the tumor comprises liver cancer and a mass ratio of kaempferol-3-O-[2-O-(6-O-E-feruloyl)-β-D-glucopyranosyl]-β-D -galactopyranose to E-6-O-(p-coumaroyl) scandoside methyl ester in combination is 1:2-1:5 or 2:1-5:1.

2. The method according to claim 1, wherein a mass ratio of kaempferol-3-O-[2-O-(6-O-E-feruloyl)-β-D-glucopyranosyl]-β-D-galactopyranose to E-6-O-(p-coumaroyl) scandoside methyl ester in combination is 1:2, 1:3, 1:4, 1:5, 2:1, 3:1, 4:1 or 5:1.

3. The method according to claim 1, wherein a mass ratio of kaempferol-3-O-[2-O-(6-O-E-feruloyl)-β-D-glucopyranosyl]-β-D-galactopyranose to E-6-O-(p-coumaroyl) scandoside methyl ester in combination is 3:1.

* * * * *